(12) United States Patent
Irvin

(10) Patent No.: US 8,251,299 B1
(45) Date of Patent: Aug. 28, 2012

(54) SCREW TOP AIR FRESHENER

(75) Inventor: Aaron Irvin, Salt Lake City, UT (US)

(73) Assignee: American Covers, Inc., Draper, UT (US)

( * ) Notice: Subject to any disclaimer, the term of this patent is extended or adjusted under 35 U.S.C. 154(b) by 93 days.

(21) Appl. No.: 12/916,038

(22) Filed: Oct. 29, 2010

(51) Int. Cl.
 *A24F 25/00* (2006.01)

(52) U.S. Cl. ............... 239/58; 239/34; 239/57; 239/59; 239/60; 220/23.83; 220/87.1; 220/676

(58) Field of Classification Search ............ 239/34, 239/53, 57–60; 220/23.83, 87.1, 288, 676
 See application file for complete search history.

(56) References Cited

U.S. PATENT DOCUMENTS

| | | |
|---|---|---|
| D176,671 S | 4/1876 | Myers |
| 1,683,545 A | 9/1928 | Harris |
| D140,109 S | 1/1945 | Pierce |
| 2,642,248 A | 6/1953 | Semon |
| 2,733,333 A | 1/1956 | Peters |
| D177,826 S | 5/1956 | Katz |
| D178,237 S | 7/1956 | Katz |
| 3,239,145 A * | 3/1966 | Russo .................. 239/58 |
| 3,456,106 A | 7/1969 | Gluschkin Mischa |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,226,944 A | 10/1980 | Stone et al. |
| D258,511 S | 3/1981 | Ashton |
| 4,280,649 A * | 7/1981 | Montealegre .................. 239/57 |
| 4,301,949 A | 11/1981 | Palson et al. |
| 4,382,548 A * | 5/1983 | van der Heijden ........... 220/87.1 |
| 4,391,781 A | 7/1983 | Van Lit |
| 4,517,326 A | 5/1985 | Cordts et al. |
| 4,549,693 A * | 10/1985 | Barlics ......................... 239/58 |

(Continued)

FOREIGN PATENT DOCUMENTS

CA 2077251 5/1993

(Continued)

OTHER PUBLICATIONS

ABOUT.COM Housekeeping, http://housekeeping.about.com/od/pr...affresh, Febrezee Noticeables, accessed Oct. 2, 2008, 2 pages.

(Continued)

*Primary Examiner* — Steven J Ganey
(74) *Attorney, Agent, or Firm* — Thorpe North & Western LLP

(57) ABSTRACT

An air freshener has a fragrant gel material in a container with a double-wall including an inner wall and an outer wall with an annular gap. A cap was a sleeve extending into the annular gap. An opening is disposed in the sleeve. The cap is movable axially with respect to the container between a raised position in which the opening in the sleeve is exposed at least partially above the double-wall to release fragrance, and a closed position in which the opening in the sleeve is disposed in the annular gap to resist release of fragrance.

20 Claims, 5 Drawing Sheets

U.S. PATENT DOCUMENTS

| | | | |
|---|---|---|---|
| 4,594,380 A | 6/1986 | Chapin et al. | |
| D286,323 S | 10/1986 | Haworth | |
| 4,638,057 A | 1/1987 | Takahashi et al. | |
| 4,649,046 A | 3/1987 | Kross | |
| 4,703,070 A | 10/1987 | Locko et al. | |
| RE32,834 E | 1/1989 | Cordts et al. | |
| 4,808,347 A | 2/1989 | Dawn | |
| 4,840,773 A | 6/1989 | Wade | |
| 4,874,129 A | 10/1989 | DiSapio et al. | |
| 4,880,690 A | 11/1989 | Szycher et al. | |
| 4,950,542 A | 8/1990 | Barker | |
| 4,968,456 A | 11/1990 | Muderlak et al. | |
| 5,008,115 A | 4/1991 | Lee et al. | |
| 5,019,434 A | 5/1991 | Matsumoto | |
| 5,050,798 A | 9/1991 | Sullivan | |
| D322,558 S | 12/1991 | Halm et al. | |
| 5,071,704 A | 12/1991 | Fischel-Ghodsian | |
| 5,114,625 A | 5/1992 | Gibson | |
| 5,178,327 A | 1/1993 | Palamand et al. | |
| 5,180,107 A | 1/1993 | Lindauer | |
| 5,193,445 A | 3/1993 | Ferguson | |
| D334,975 S | 4/1993 | Bunce et al. | |
| 5,220,636 A | 6/1993 | Chang | |
| D338,519 S | 8/1993 | Peterson | |
| 5,234,162 A | 8/1993 | Sullivan | |
| D349,157 S | 7/1994 | Rymer | |
| 5,368,822 A | 11/1994 | McNeil | |
| 5,407,642 A | 4/1995 | Lord | |
| 5,422,078 A | 6/1995 | Colon | |
| D367,526 S | 2/1996 | Bignon | |
| D373,626 S | 9/1996 | Patel et al. | |
| D375,350 S | 11/1996 | Patel et al. | |
| 5,595,194 A | 1/1997 | Talbot | |
| D380,258 S | 6/1997 | Muller et al. | |
| 5,651,522 A | 7/1997 | Davis et al. | |
| 5,683,285 A | 11/1997 | Wong | |
| 5,695,692 A | 12/1997 | Kennedy | |
| 5,704,832 A | 1/1998 | Borrell | |
| D390,941 S | 2/1998 | Cessaroni et al. | |
| 5,762,549 A | 6/1998 | Scheuer et al. | |
| 5,780,527 A | 7/1998 | O'Leary | |
| 5,794,767 A | 8/1998 | Wilson | |
| 5,820,791 A | 10/1998 | Canale | |
| D400,662 S | 11/1998 | Davis | |
| 5,845,847 A | 12/1998 | Martin et al. | |
| 5,860,552 A | 1/1999 | Culhane et al. | |
| 5,861,128 A | 1/1999 | Vick et al. | |
| D404,957 S | 2/1999 | Cheris et al. | |
| 5,871,765 A | 2/1999 | Johnson et al. | |
| 5,899,382 A | 5/1999 | Hayes et al. | |
| D410,540 S | 6/1999 | Pinchuk | |
| D415,267 S | 10/1999 | Kauzlarich et al. | |
| 5,988,520 A * | 11/1999 | Bitner | 239/60 |
| 6,044,202 A | 3/2000 | Junkel | |
| D424,677 S | 5/2000 | Chen | |
| D425,190 S | 5/2000 | Morikawa | |
| 6,111,055 A | 8/2000 | Berger et al. | |
| 6,123,906 A | 9/2000 | Farmer | |
| D432,222 S | 10/2000 | Rymer et al. | |
| 6,190,607 B1 | 2/2001 | Farmer | |
| 6,191,197 B1 | 2/2001 | Wang et al. | |
| 6,197,263 B1 | 3/2001 | Blount | |
| 6,202,938 B1 | 3/2001 | Collier | |
| D440,294 S | 4/2001 | Bilek | |
| D441,441 S | 5/2001 | Upson | |
| 6,264,887 B1 | 7/2001 | Farmer | |
| 6,291,371 B1 | 9/2001 | Shefer et al. | |
| 6,309,715 B1 | 10/2001 | Lindauer et al. | |
| 6,325,475 B1 | 12/2001 | Hayes et al. | |
| 6,357,260 B1 | 3/2002 | Lutz | |
| 6,374,044 B1 | 4/2002 | Freidel | |
| 6,375,966 B1 | 4/2002 | Maleeny et al. | |
| 6,379,689 B1 | 4/2002 | Aguadisch | |
| 6,416,043 B1 | 7/2002 | Elsenbraun | |
| 6,514,467 B1 | 2/2003 | Bulsink et al. | |
| D472,968 S | 4/2003 | Christianson | |
| D478,379 S | 8/2003 | Talenton et al. | |
| D478,973 S | 8/2003 | Wagner | |
| D479,592 S | 9/2003 | Lammel et al. | |
| D485,343 S | 1/2004 | Wu | |
| D487,504 S | 3/2004 | Yuen | |
| 6,712,286 B2 | 3/2004 | Baxter et al. | |
| D488,214 S | 4/2004 | Quantin | |
| D488,548 S | 4/2004 | Lablaine | |
| D491,257 S | 6/2004 | Picken, Jr. | |
| D491,798 S | 6/2004 | Buthier | |
| D496,720 S | 9/2004 | Dudley | |
| 6,800,252 B1 | 10/2004 | Jedzinski | |
| 6,885,811 B2 | 4/2005 | He et al. | |
| D504,943 S | 5/2005 | Dudley | |
| D507,341 S | 7/2005 | Taylor | |
| D511,568 S | 11/2005 | Wheatley | |
| D514,679 S | 2/2006 | Wheatley | |
| D515,192 S | 2/2006 | Smith et al. | |
| 7,025,283 B2 | 4/2006 | Torres | |
| 7,055,764 B1 | 6/2006 | Martinez et al. | |
| 7,061,386 B2 | 6/2006 | Seresini | |
| 7,137,570 B2 | 11/2006 | Wheatley et al. | |
| 535,379 A1 | 1/2007 | Hundertmark | |
| 7,159,792 B2 | 1/2007 | Wheatley et al. | |
| D544,080 S | 6/2007 | Carlson | |
| D544,594 S | 6/2007 | Zobele | |
| D544,953 S | 6/2007 | Kee | |
| D546,432 S | 7/2007 | Hundertmark | |
| 7,243,859 B2 | 7/2007 | Caserta et al. | |
| D550,345 S | 9/2007 | Weggelaar | |
| D554,746 S | 11/2007 | Davis et al. | |
| 7,293,719 B2 | 11/2007 | Wheatley | |
| D565,162 S | 3/2008 | Carlson | |
| 7,344,123 B2 | 3/2008 | Pankhurst et al. | |
| D565,715 S | 4/2008 | Wu | |
| D573,706 S | 7/2008 | Zlotnik et al. | |
| D574,941 S | 8/2008 | Weggelaar | |
| D580,039 S | 11/2008 | Zlotnik et al. | |
| D585,129 S | 1/2009 | Huang | |
| D585,971 S | 2/2009 | Carrizales | |
| D591,415 S | 4/2009 | Wu | |
| D593,670 S | 6/2009 | Valentino et al. | |
| D594,954 S | 6/2009 | Wheatley | |
| 7,544,332 B2 | 6/2009 | De Silva et al. | |
| D598,531 S | 8/2009 | Irvin | |
| D607,983 S | 1/2010 | Irvin | |
| 7,651,666 B2 | 1/2010 | Adair et al. | |
| 7,670,566 B2 | 3/2010 | Adair et al. | |
| 7,687,037 B2 | 3/2010 | Wheatley | |
| 7,687,038 B2 | 3/2010 | Wheatley | |
| 7,780,094 B2 | 8/2010 | Caserta et al. | |
| D629,881 S | 12/2010 | Valention et al. | |
| D631,954 S | 2/2011 | Bertassi et al. | |
| D633,610 S | 3/2011 | Wu | |
| D642,668 S | 8/2011 | Lablain | |
| D647,186 S | 10/2011 | Chan et al. | |
| D649,237 S | 11/2011 | Bilko et al. | |
| 2003/0097936 A1 | 5/2003 | Maleeny et al. | |
| 2003/0199421 A1 | 10/2003 | Copfer | |
| 2004/0265164 A1 | 12/2004 | Woo et al. | |
| 2005/0127538 A1 | 6/2005 | Fabrega | |
| 2005/0169793 A1 | 8/2005 | Wheatley et al. | |
| 2006/0078477 A1 | 4/2006 | Althouse et al. | |
| 2006/0279008 A1 | 12/2006 | Jursich | |
| 2007/0057084 A1 | 3/2007 | Vieira | |
| 2007/0160492 A1 | 7/2007 | Spector | |
| 2008/0128925 A1 | 6/2008 | Pankhurst et al. | |
| 2009/0010813 A1 | 1/2009 | Wang et al. | |
| 2010/0010409 A1 | 1/2010 | Bejarano | |
| 2010/0065654 A1 | 3/2010 | Wheatley et al. | |
| 2010/0187327 A1 | 7/2010 | Irvin | |

FOREIGN PATENT DOCUMENTS

| | | |
|---|---|---|
| EP | 0 348 970 | 1/1990 |
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2004/078219 | 9/2004 |

| WO | WO 2006/010282 | 2/2006 |
| WO | WO 2006/084160 | 8/2006 |
| ZA | 20004637 | 9/2000 |

OTHER PUBLICATIONS

Aromate E-News, Innovation in Novelty Fragrance, Http://209.85.173.104/seasrch?qcach..., accessed Oct. 8, 2008, 2 pages.

Ecrater, www.ecrater.com/product.hp?..., Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

http://shop.advanceautoparts.com/webapp/wcs/stores/servlet/product_6170795-P_N3004...Advance Auto Part; Arometrics Dual-Scent Vent—Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark, CA 2003 copyright date on package.

Scents & Sprays, www.scentsandsprays.com/ya..., Yankee Autumn Bounty Electric 2 Home Air Fresheners, copyright 2001-2008 scentsandsprays.com, accessed Oct. 2, 2008, 1 page.

U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/915,983, filed Oct. 29, 2010; Alan J. Wheatley.
U.S. Appl. No. 12/979,763, filed Dec. 28, 2010; Aaron Irvin.
U.S. Appl. No. 12/979,795, filed Dec. 28, 2010; Aaron Irvin.
UU.S. Appl. No. 12/979,813, filed Dec. 28, 2010; Aaron Irvin.
U.S. Appl. No. 13/009,574, filed Jan. 19, 2011; Alan J. Wheatley.
U.S. Appl. No. 29/378,112, filed Oct. 29, 2010; Nathaniel Finlay.
U.S. Appl. No. 29/378,116, filed Oct. 29, 2010; Aaron Irvin.
www.4imprint.com/EXEC/DETAIL/FROMPRODUCTGROUP/~SKU100300/~CA100300.htm, Hot Rod Vent Stick Air Freshener (it..., accessed Aug. 12, 2008, 2 pages.

www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

U.S. Appl. No. 12/623,007, filed Nov. 20, 2009; Alan J. Wheatley; Notice of Allowance issued Nov. 28, 2012.

U.S. Appl. No. 12/623,007, filed Nov. 20, 2009; Alan J. Wheatley; office action issued Jul. 29, 2011.

U.S. Appl. No. 29/394,683, filed Jun. 20, 2011; Alan J. Wheatley; notice of allowance issued Jun. 20, 2011.

U.S. Appl. No. 13/191,966, filed Jul. 27, 2011; Aaron Irvin.
U.S. Appl. No. 29/178,112, filed Oct. 29, 2010; Nathaniel Finlay; Notice of Allowance issued Mar. 29, 2012.

U.S. Appl. No. 29/415,538, filed Mar. 9, 2012; Aaron Irvin; Notice of Allowance issued May 29, 2012.

* cited by examiner

SCREW TOP AIR FRESHENER

BACKGROUND

1. Field of the Invention

The present invention relates generally to air fresheners.

2. Related Art

Some air fresheners provide a fragrant material in a can with a lid, which when removed allows the fragrance to escape, but also exposes the fragrant material in the entire can to debris, escape, children and/or pets. It will be appreciated the fragrant material can be harmful if ingested and/or a skin or eye irritant. In addition, it will be appreciated that the fragrant material can be harmful to surfaces, such as by staining.

Another air freshener can has a lid with overlapping upward aperture that can turn to align the apertures.

SUMMARY OF THE INVENTION

It has been recognized that it would be advantageous to develop an air freshener to selectively release scent. In addition, it has been recognized that it would be advantageous to develop an air freshener that resists tampering and/or fouling.

The invention provides an air freshener device with a container containing a fragrant gel material from which a fragrance permeates over time. The container has a cylindrical-shaped perimeter with a double-wall, including an inner wall and an outer wall, and defines an annular gap between the double-wall. The container also has a bottom wall with the bottom wall and inner wall defining a reservoir containing the fragrant gel material. A screw thread is formed on an exterior surface of the inner wall. A cap is secured to the container and covers the reservoir. A cylindrical sleeve extends from the cap into the annular gap between the double-wall. A plurality of apertures is disposed in the cylindrical sleeve. A screw thread is formed on an interior surface of the sleeve, and engages the screw thread on the exterior surface of the inner wall. Rotation of the cap moves the cap axially with respect to the container, including a raised position in which the plurality of apertures in the cylindrical sleeve are exposed to release fragrance, and a closed position in which the plurality of apertures in the cylindrical sleeve are disposed in the annular gap to resist release of fragrance.

In accordance with another aspect, the invention provides an air freshener device with a container containing a fragrant gel material from which a fragrance permeates over time. The container has a double-wall including an inner wall and an outer wall, and defines an annular gap between the double-wall. The container has a bottom wall with the bottom wall and inner wall defining a reservoir containing the fragrant gel material. A cap is carried by the container and covers the reservoir. A sleeve extends from the cap into the annular gap between the double-wall. At least one opening is disposed in the sleeve. The cap is movable axially with respect to the container between a raised position in which the at least one opening in the sleeve is exposed at least partially above the double-wall to release fragrance, and a closed position in which the at least one opening in the sleeve is disposed in the annular gap to resist release of fragrance.

In accordance with another aspect, the invention provides an air freshener device with a container containing a fragrant material from which a fragrance permeates over time. The container has a double-wall including an inner wall and an outer wall, and defines a gap between the double-wall. The container has a bottom wall with the bottom wall and inner wall defining a reservoir containing the fragrant material. The inner wall is formed of a material that is at least translucent and that resists reacting with the fragrant material. The outer wall is formed of a transparent material that is reactable with the fragrant material, but separated from the fragrant material by the inner wall. A cap is carried by the container and covers the reservoir. A sleeve extends from the cap into the gap between the double-wall. At least one opening is disposed in the sleeve. The cap is movable axially with respect to the container between a raised position in which the at least one opening in the sleeve is exposed at least partially above the double-wall to release fragrance, and a closed position is which the at least one opening in the sleeve is disposed in the annular gap to resist release of fragrance.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Figure 1:
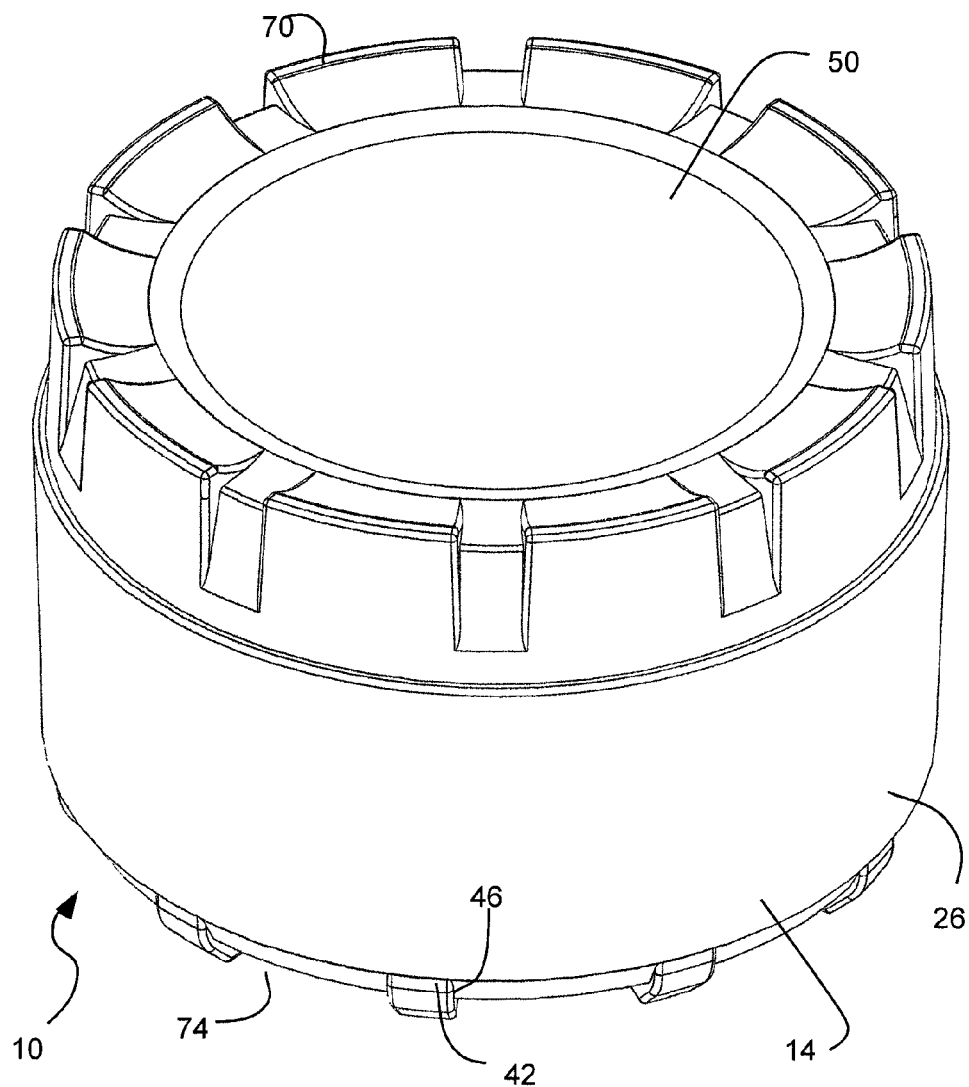
FIG. 1 is a perspective view of an air freshener device in accordance with an embodiment of the present invention.
Figure 2:
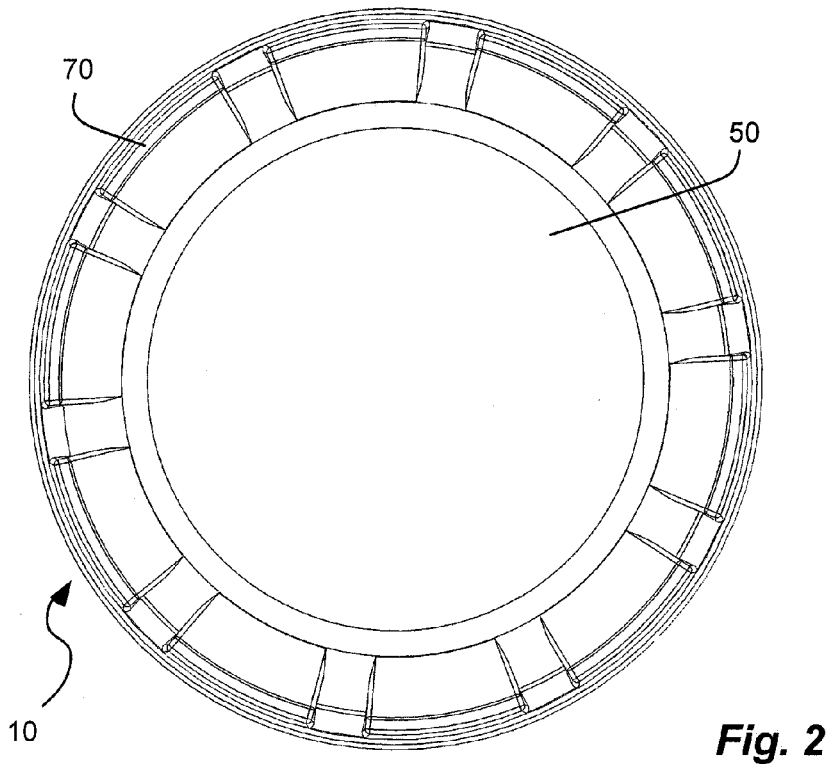
FIG. 2 is a top view of the air freshener device of FIG. 1.
Figure 3:
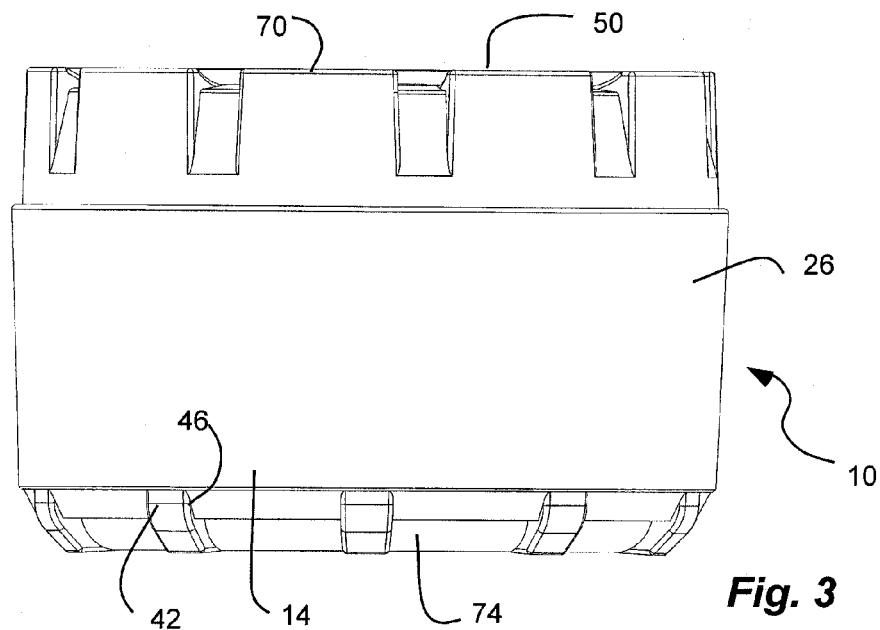
FIG. 3 is a side view of the air freshener device of FIG. 1.
Figure 4:
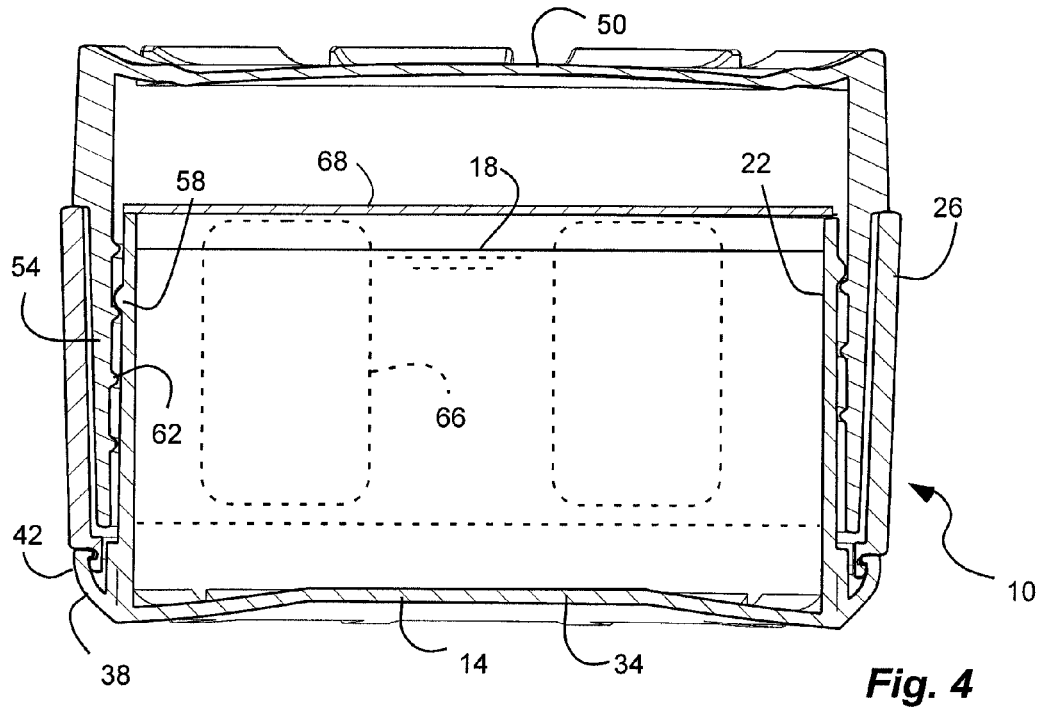
FIG. 4 is a cross-sectional side view of the air freshener device of FIG. 1, shown is a closed position with a fragrant material and a release liner.

As illustrated in FIG. 1, an air freshener device, indicated generally at 10, in an example implementation in accordance with the invention is shown. The air freshener can provide a scented gel material in a clear container with a cap that selectively exposes the scented gel material or that axially displaces with respect to the container to selectively increase a gap between the cap and the container to control scent release. The air freshener can provide a desired and/or aesthetically pleasing scent, fragrance, aroma or neutralizing agent. Air fresheners are one example of a field that can benefit from the present invention.

The air freshener 10 includes a container 14 that contains a fragrant material, such as a fragrant gel material 18, from which a fragrance permeates over time. The fragrant gel material can be a water based gel. The container 14 can have a cylindrical shape or a cylindrical-shaped perimeter to accommodate rotation as discussed below. In addition, the container 14 can have a double-wall, including an inner wall 22 and an outer wall 26. An annular gap 30 is formed between the double-wall, or inner and outer walls. The inner and outer walls can have a cylindrical shape. Furthermore, the container can have a bottom wall 34 attached at a bottom of the double-wall, or inner and outer walls. The bottom wall 34 and inner wall 22 can define a reservoir containing the fragrant gel material 18. The reservoir formed by the bottom and inner walls can be an open top cylinder with an unobstructed circular open top to maximize the exposed surface area of the fragrant gel material, and thus scent release. The inner wall 22 can be formed of, or can include, a material that resists reacting with the fragrant gel material, such as polypropylene. Similarly, the bottom wall 34 can be formed of the same material as the inner wall that resists reaction with the fragrant gel material. The inner wall and bottom wall can be a single, integral, monolithic piece that is formed together, such as of plastic in an injection molding process. The outer wall 26, however, can be formed of, or can include, a material that is reactable with the fragrant gel material, such as polystyrene, but is separated from the fragrant gel material by the inner wall 22 and gap 30. Thus, the inner and outer walls can be formed of, or can include, different materials. The inner wall 22 or material thereof can be at least translucent. The outer wall 26 or material thereof can be transparent. Thus, the fragrant gel material can be viewed through the double-wall, or inner and outer walls, to ascertain the amount or level of fragrant gel material remaining in the container. It will be appreciated that the fragrant gel material can dissolve or otherwise dissipate over time.

The container 14 can also have a bottom annular lip 38 protruding laterally or radially outwardly from a bottom of the inner wall 22 or as a continuation of the bottom wall 34. The outer wall 26 can be an annular cylindrical band. A bottom or bottom rim of the outer wall or annular band can be coupled to or attached to the bottom annular lip 38. The bottom annular lip 38 has an array of protrusions 42 circumscribing the bottom annular lip. The bottom or bottom rim of the outer wall 26 has an array of indentations 46 circumscribing the bottom rim and mating with the array of protrusions 42 of the bottom annular lip 38. The mating indentations and protrusions can resist rotation of the outer wall 26 or annular band with respect to the inner wall 22 and container.

The container and reservoir can also have a puck or puck-like shape with a diameter greater than a height to maximize surface area exposure, and thus scent release, of the fragrant material.

Figure 5:
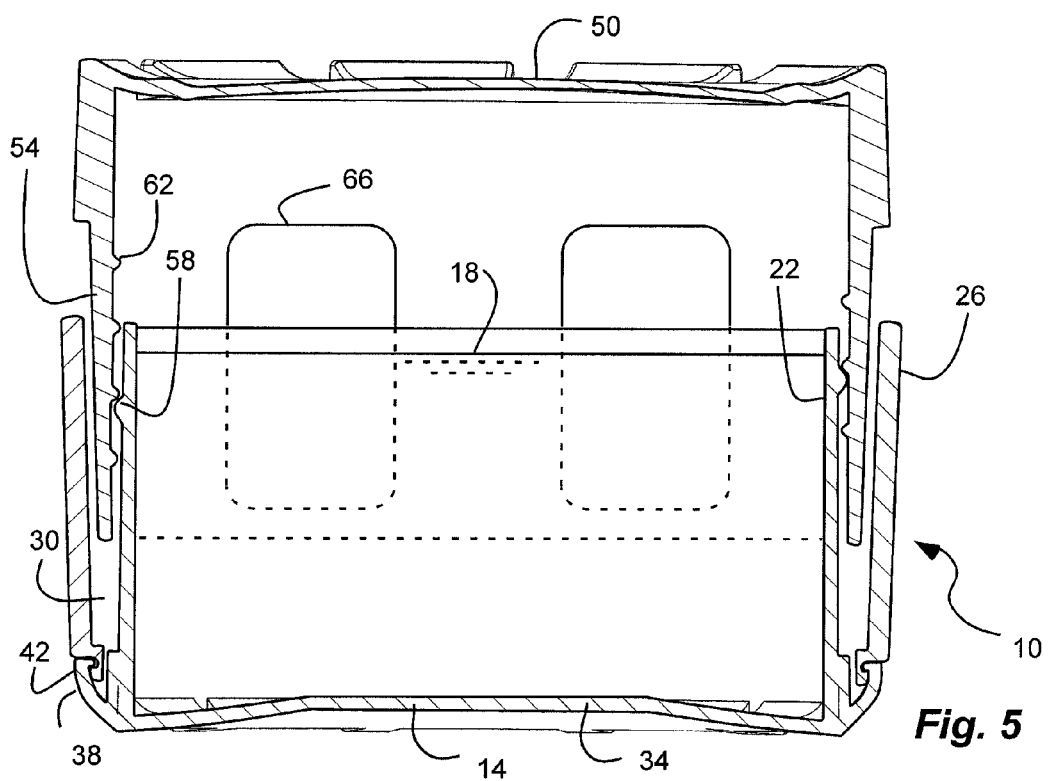
FIG. 5 is a cross-sectional side view of the air freshener device of FIG. 1, shown in a raised position with the fragrant material.
Figure 6:
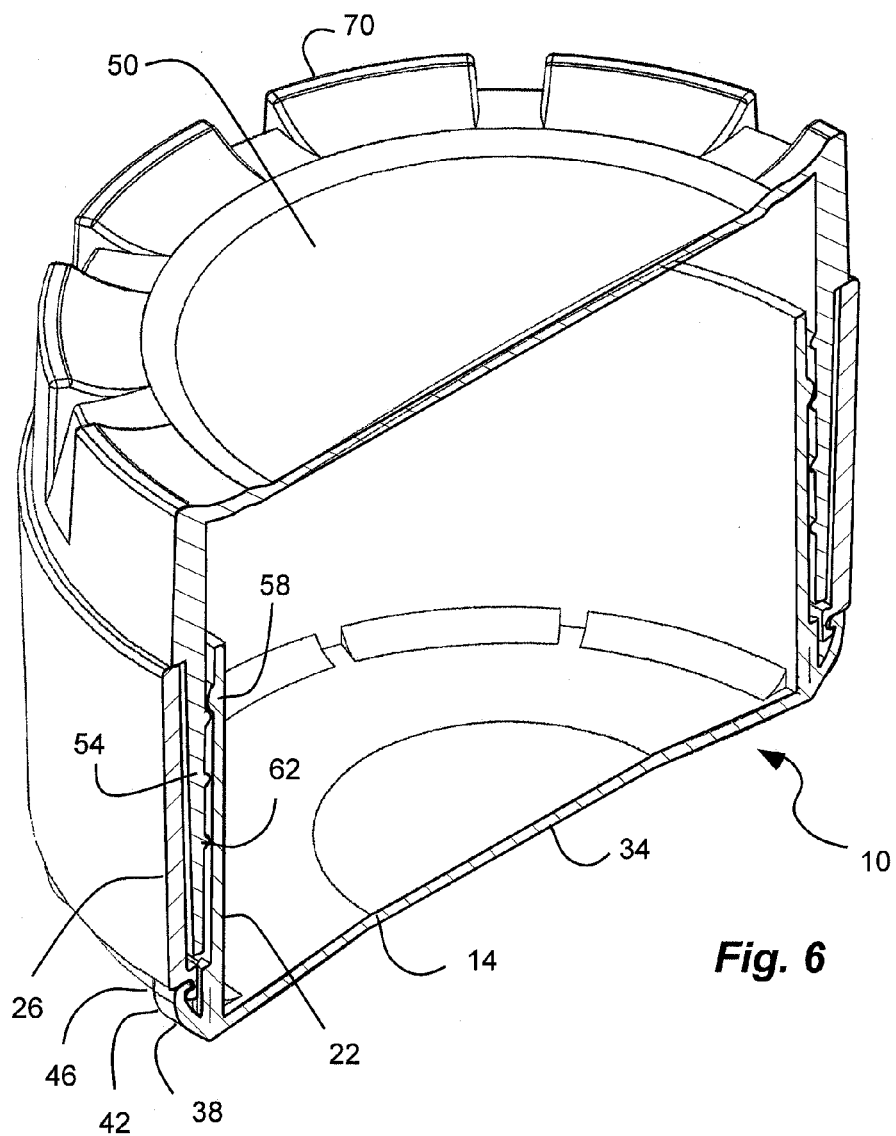
FIG. 6 is a cross-sectional perspective view of the air freshener device of FIG. 1.
Figure 7:
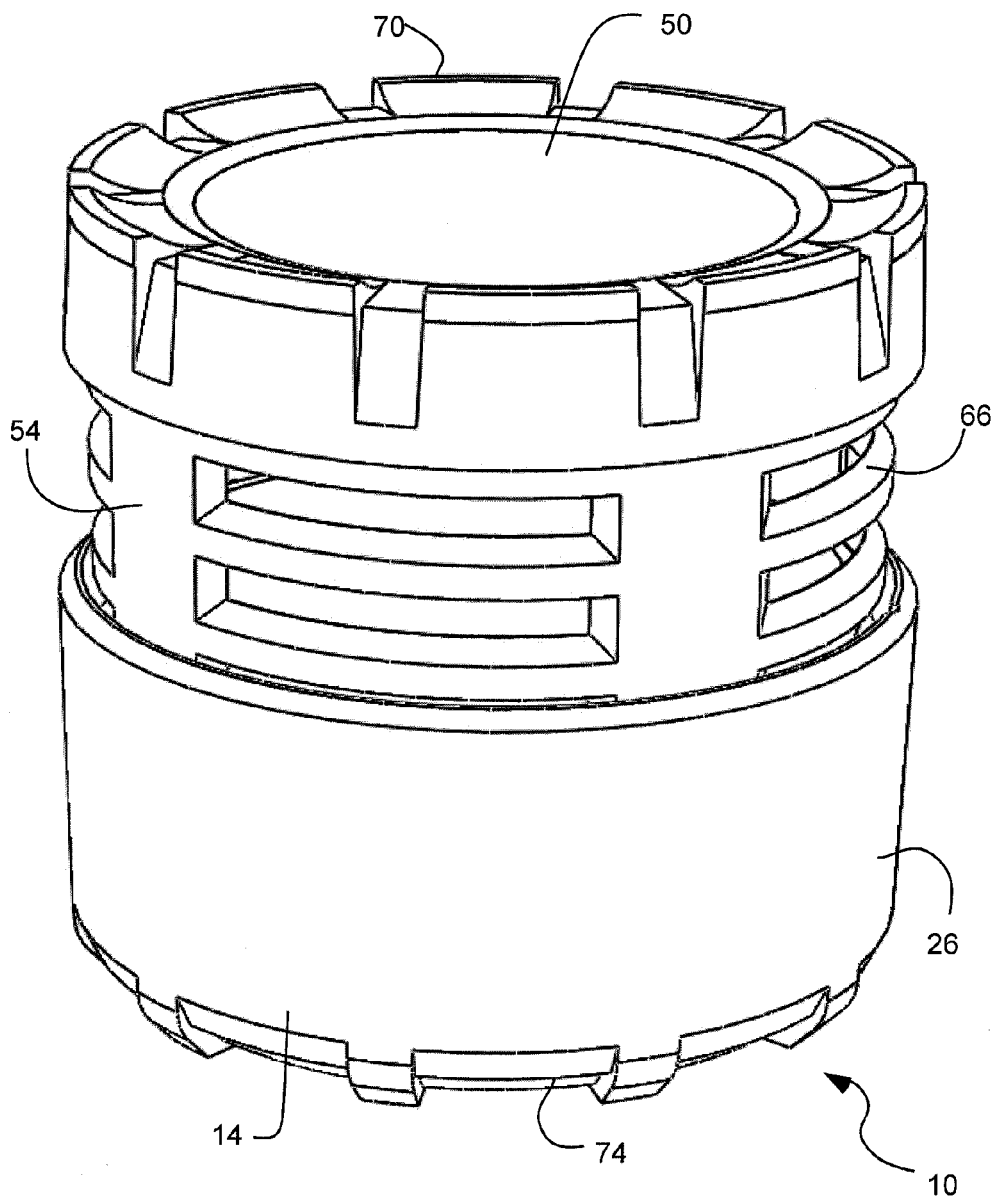
FIG. 7 is a perspective view of the air freshener device of FIG. 1, shown in a raised position.

A cap 50 is secured to the container 14 and covers the reservoir and the fragrant material therein. The cap 50 can have an annular rim that abuts an upper rim of the outer wall 26 and or inner wall in a closed position. The outer perimeter of the cap can be substantially flush with the outer perimeter of the outer wall 26. The cap 50 can be part of the container 14. A cylindrical sleeve 54 can extend from the cap 50 into the annular gap 30 between the double-wall, or inner and outer walls. The cap 50 can displace axially away from the container 14 and maintain its position over the container held by the sleeve 54. A screw thread 58, such as an exterior or male thread, can be formed on an exterior surface of the inner wall 22. The exterior screw thread 58 can for a single complete rotation about the inner wall 22. A screw thread 62, such as an interior or female thread, can be formed on an interior surface of the sleeve 54. The interior screw thread 62 can be segmented or interrupted by the holes or apertures. The screw threads engage such that rotation of the cap 50 moves the cap axially with respect to the container 14, including a raised position as shown in FIGS. 5 and 7, and a closed position as shown in FIGS. 1, 3, 4 and 6. The sleeve 54 can be flexible and resilient, and the internal screw threads 62 can be shallow or thin, such that the sleeve can pulled directly out of the annular gap 30. The cap and sleeve can be formed of ABS.

One or more holes, slots or apertures 66 can be formed in or defined in the sleeve 54. In the raised position, the one or more apertures or holes 66 of the sleeve 54 are exposed above the rim allowing the release of fragrance. In the closed position, the one or more apertures or holes 66 of the sleeve are disposed in the annular gap 30 to resist release of fragrance. The cap 50 covers a top of the container or reservoir while the openings or apertures 54 provide lateral scent release, and together resist tampering by children or animals while still allowing scent release. In addition, the cap and lateral openings or apertures also resist fouling or debris from entering the container or reservoir, and thus the fragrant gel material.

The cap 50 and cylindrical sleeve 54 can be removable from and replaceable with the container 14. A release liner 68 (FIG. 4) can be initially releasably coupled to a top rim of the inner wall 22 to seal the reservoir. Thus, in use, the cap can be removed to remove the release liner, and the cap replaced.

In addition, the cap can have an upper rim with an array of protrusions 70 circumscribing the upper rim. The bottom wall 34 can have a bottom rim with an array of indentations 74 circumscribing the bottom rim and matching the array of protrusions 70 of the upper rim so that the bottom rim mates with an upper rim of another air freshener device stacked thereon.

In use, the air freshener 10 can be provided, shipped and sold with the release liner 68 affixed to the rim of the inner wall 22 to seal the fragrant gel material in the reservoir. A plurality of the air fresheners can be stacked together for sale, or in use, with protrusions 70 of the upper rim of the cap matching, nesting or engaging the indentations 74 in the bottom rim of an adjacent stacked air freshener. (It will be appreciated that indentations can be formed between the protrusions 70, and protrusions can be formed between the indentations 74. It will also be appreciated that the protrusions 70 and indentations 74 can be reversed.) The cap 50 and sleeve 54 can be removed from the container, either by unscrewing the cap, or by pulling the cap, and thus the sleeve directly from the annular gap. The release liner 68 can be peeled from the upper rim of the inner wall exposing the fragrant gel material. The cap and sleeve can be replaced on the container, again such as by screwing the cap, or by pushing the sleeve directly into the annular gap. The cap can then be selectively raised or lowered (or closed) to stop or control the amount of scent released.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device, comprising:
   a) a container containing a fragrant gel material from which a fragrance permeates over time;
   b) the container having a cylindrical-shaped perimeter with a double-wall including an inner wall and an outer wall, and defining an annular gap between the double-wall;
   c) the container having a bottom wall with the bottom wall and inner wall defining a reservoir containing the fragrant gel material;
   d) a screw thread formed on an exterior surface of the inner wall;
   e) a cap secured to the container and covering the reservoir;
   f) a cylindrical sleeve extending from the cap into the annular gap between the double-wall;
   g) a plurality of apertures in the cylindrical sleeve; and
   h) a screw thread formed on an interior surface of the sleeve and engaging the screw thread on the exterior surface of the inner wall such that rotation of the cap moves the cap axially with respect to the container including a raised position in which the plurality of apertures in the cylindrical sleeve are exposed to release fragrance, and a closed position in which the plurality of apertures in the cylindrical sleeve are disposed in the annular gap to resist release of fragrance.

2. A device in accordance with claim 1, further comprising:
a) a release liner releasably coupled to a top rim of at the inner wall; and
b) the cap and cylindrical sleeve being removable from and replaceable with the container.

3. A device in accordance with claim 1, wherein the cap has an upper rim with an array of protrusions circumscribing the upper rim; wherein the bottom wall has a bottom rim with an array of indentations circumscribing the bottom rim matching the array of protrusions of the upper rim so that the bottom rim mates with an upper rim of another air freshener device stacked thereon.

4. A device in accordance with claim 1, wherein the outer wall includes a different material than the inner wall.

5. A device in accordance with claim 4, wherein the inner wall is formed of at least a translucent material that resists reacting with the fragrant material; and wherein the outer wall is formed of a transparent material that is reactable with the fragrant material.

6. A device in accordance with claim 1, wherein the container has a bottom annular lip protruding laterally from a bottom of the inner wall; and wherein the outer wall is an annular band with a bottom rim secured to the bottom annular lip.

7. A device in accordance with claim 6, wherein the bottom annular lip has an array of protrusions circumscribing the bottom annular lip of the inner wall; and wherein the bottom rim of the outer wall has an array of indentations circumscribing the bottom rim and mating with the array of protrusions of the bottom annular lip.

8. A device in accordance with claim 1, wherein the cap has an annular rim that abuts an upper rim of the outer wall in the closed position; and wherein an outer perimeter of the cap is substantially flush with an outer perimeter of the outer wall of the container.

9. An air freshener device, comprising:
a) a container containing a fragrant gel material from which a fragrance permeates over time;
b) the container having a double-wall including an inner wall and an outer wall, and defining an annular gap between the double-wall;
c) the container having a bottom wall with the bottom wall and inner wall defining a reservoir containing the fragrant gel material;
d) a cap carried by the container and covering the reservoir;
e) a sleeve extending from the cap into the annular gap between the double-wall;
f) at least one opening in the sleeve; and
g) the cap movable axially with respect to the container between a raised position in which the at least one opening in the sleeve is exposed at least partially above the double-wall to release fragrance, and a closed position in which the at least one opening in the sleeve is disposed in the annular gap to resist release of fragrance.

10. A device in accordance with claim 9, further comprising:
a) a release liner releasably coupled to a top rim of the inner wall; and
b) the cap and sleeve being removable from and replaceable with the container.

11. A device in accordance with claim 9, wherein the cap has an upper rim with an array of protrusions circumscribing the upper rim; wherein the bottom wall has a bottom rim with an array of indentations circumscribing the bottom rim matching the array of protrusions of the upper rim so that the bottom rim mates with an upper rim of another air freshener device stacked thereon.

12. A device in accordance with claim 9, wherein the outer wall includes a different material than the inner wall.

13. A device in accordance with claim 12 wherein the inner wall is formed of at least a translucent material that resists reacting with the fragrant material; and wherein the outer wall is formed of a transparent material that is reactable with the fragrant material.

14. A device in accordance with claim 9, wherein the container has a bottom annular lip protruding laterally from a bottom of the inner wall; and wherein the outer wall is an annular band with a bottom rim secured to the bottom annular lip.

15. A device in accordance with claim 14, wherein the bottom annular lip has an array of protrusions circumscribing the bottom annular lip; and wherein the bottom rim of the outer wall has an array of indentations circumscribing the bottom rim and mating with the array of protrusions of the bottom annular lip.

16. A device in accordance with claim 9, wherein the cap has an annular rim that abuts an upper rim of the outer wall in the closed position; and wherein an outer perimeter of the cap is substantially flush with an outer perimeter of the outer wall of the container.

17. An air freshener device, comprising:
a) a container containing a fragrant material from which a fragrance permeates over time;
b) the container having a double-wall including an inner wall and an outer wall, and defining a gap between the double-wall;
c) the container having a bottom wall with the bottom wall and inner wall defining a reservoir containing the fragrant material;
d) the inner wall is formed of a material that is at least translucent and that resists reacting with the fragrant material;
e) the outer wall is formed of a transparent material that is reactable with the fragrant material but separated from the fragrant material by the inner wall;
f) a cap carried by the container and covering the reservoir;
g) a sleeve extending from the cap into the gap between the double-wall;
h) at least one opening in the sleeve; and
i) the cap movable axially with respect to the container between a raised position in which the at least one opening in the sleeve is exposed at least partially above the double-wall to release fragrance, and a closed position in which the at least one opening in the sleeve is disposed in the annular gap to resist release of fragrance.

18. A device in accordance with claim 17 further comprising:
a) a release liner releasably coupled to a top rim of the inner wall; and
b) the cap and cylindrical sleeve being removable from and replaceable with the container.

19. A device in accordance with claim 17, wherein the cap has an upper rim with an array of protrusions circumscribing the upper rim; wherein the bottom wall has a bottom rim with an array of indentations circumscribing the bottom rim matching the array of protrusions of the upper rim so that the bottom rim mates with an upper rim of another air freshener device stacked thereon.

20. A device in accordance with claim 17, wherein the container has a bottom annular lip protruding laterally from a bottom of the inner wall; wherein the outer wall is an annular band with a bottom rim secured to the bottom annular lip; wherein the bottom annular lip has an array of protrusions circumscribing the bottom annular lip; and wherein the bottom rim of the outer wall has an array of indentations circumscribing the bottom rim mating with the array of protrusions of the bottom annular lip.

* * * * *